US012791854B2

(12) United States Patent
Koizumi

(10) Patent No.: US 12,791,854 B2
(45) Date of Patent: Nov. 10, 2026

(54) IMAGE DISPLAY SYSTEM AND IMAGE DISPLAY METHOD

(71) Applicant: Sony Interactive Entertainment Inc., Tokyo (JP)

(72) Inventor: Makoto Koizumi, Saitama (JP)

(73) Assignee: Sony Interactive Entertainment Inc., Tokyo (JP)

( * ) Notice: Subject to any disclaimer, the term of this patent is extended or adjusted under 35 U.S.C. 154(b) by 478 days.

(21) Appl. No.: 18/322,022

(22) Filed: May 23, 2023

(65) Prior Publication Data

US 2023/0393403 A1 Dec. 7, 2023

(30) Foreign Application Priority Data

Jun. 6, 2022 (JP) ................................. 2022-091633

(51) Int. Cl.

| | |
|---|---|
| ***G02B 27/00*** | (2006.01) |
| ***A61B 3/10*** | (2006.01) |
| ***G02B 27/01*** | (2006.01) |

(52) U.S. Cl.

CPC ........ *G02B 27/0093* (2013.01); *A61B 3/1005* (2013.01); *G02B 2027/0187* (2013.01)

(58) Field of Classification Search

CPC ........ G02B 27/0093; G02B 2027/0187; A61B 3/1005

See application file for complete search history.

(56) References Cited

U.S. PATENT DOCUMENTS

| | | | | |
|---|---|---|---|---|
| 8,269,692 | B2 | 9/2012 | Sugiyama | |
| 11,112,865 | B1 * | 9/2021 | Fix | G02B 27/0093 |
| 2010/0103077 | A1 | 4/2010 | Sugiyama | |
| 2012/0113092 | A1 * | 5/2012 | Bar-Zeev | G06T 19/006 345/419 |
| 2016/0270656 | A1 * | 9/2016 | Samec | A61B 5/1455 |
| 2018/0239136 | A1 * | 8/2018 | Ishikawa | G06F 3/013 |
| 2019/0295507 | A1 * | 9/2019 | Abuelsaad | A61B 3/111 |
| 2022/0155599 | A1 * | 5/2022 | Lychagov | G01B 9/02004 |
| 2023/0034562 | A1 * | 2/2023 | Jiang | G06F 3/1423 |

FOREIGN PATENT DOCUMENTS

| | | | | |
|---|---|---|---|---|
| CN | 102125422 A | * | 7/2011 | |
| CN | 217787507 U | * | 11/2022 | G02B 27/0172 |
| WO | 2009066465 A1 | | 5/2009 | |

OTHER PUBLICATIONS

Mitsuru Sugawara: "Proceedings of SPIE: Every aspect of advanced retinal imaging laser eyewear: principle, free focus, resolution, laser safety, and medical welfare applications" Proc. SPIE 10545, MOEMS and Miniaturized Systems XVII, 105450O, 19 pages, Feb. 22, 2018 (for relevancy see Instant specification).

* cited by examiner

*Primary Examiner* — George G. King

(74) *Attorney, Agent, or Firm* — Kilpatrick Townsend & Stockton LLP

(57) ABSTRACT

Disclosed is an image display system including an eyeball state acquisition section that acquires information regarding a state of an eye of a user, a beam control section that adjusts, according to the information regarding the state of the eye, a beam state of image laser light for forming pixels of a display image, and an image projection section that projects the image laser light onto a retina of the user.

17 Claims, 12 Drawing Sheets

14b

FIG. 5
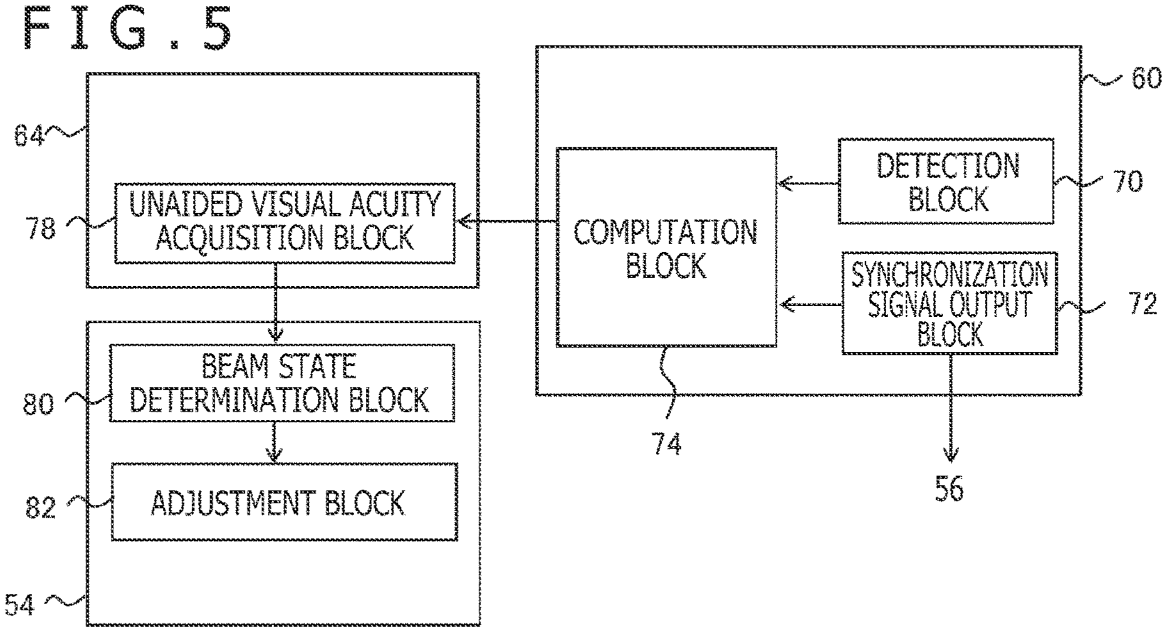
FIG. 6
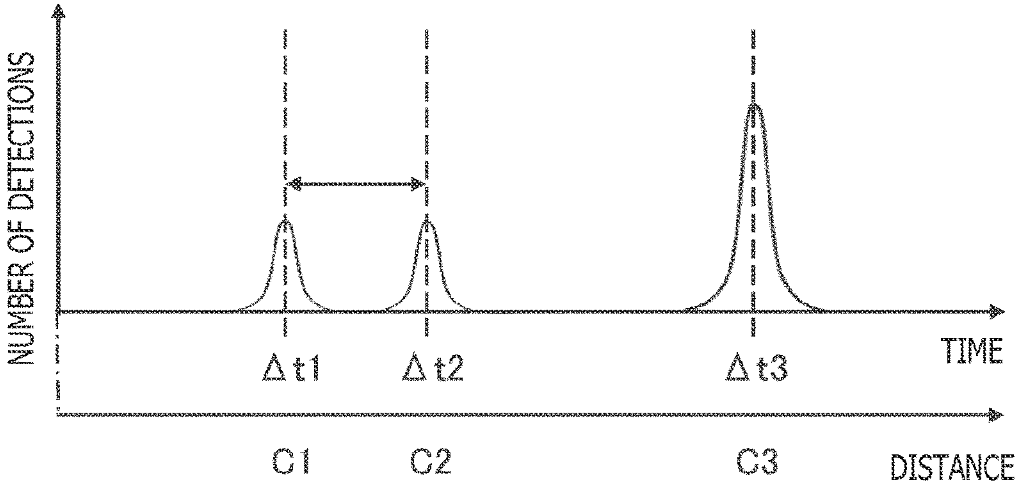
FIG. 7
| CRYSTALLINE LENS THICKNESS (mm) | UNAIDED VISUAL ACUITY |
|---|---|
| 4.7 | 0.1 |
| 4.3 | 0.5 |
| 4.0 | 1.0 |
| | |
110

| UNAIDED VISUAL ACUITY | BEAM DIAMETER (mm) | NUMERICAL APERTURE |
|---|---|---|
| 0.1 | 0.8 | −0.000 |
| 0.5 | 1.2 | −0.003 |
| 1.0 | 1.5 | −0.001 |
| | | |

FIG.15

| DISTANCE RANGE (m) | RESOLUTION |
|---|---|
| $0 \leqq D < 1$ | HIGH |
| $1 \leqq D < 5$ | MEDIUM |
| $5 \leqq D$ | LOW |
| | |

160

FIG. 16
| DISTANCE RANGE (m) | BEAM DIAMETER (mm) | NUMERICAL APERTURE |
|---|---|---|
| 0≦D<1 | 1.5 | −0.000 |
| 1≦D<5 | 1.0 | −0.003 |
| 5≦D | 0.5 | −0.045 |
| | | |
170
FIG. 17A
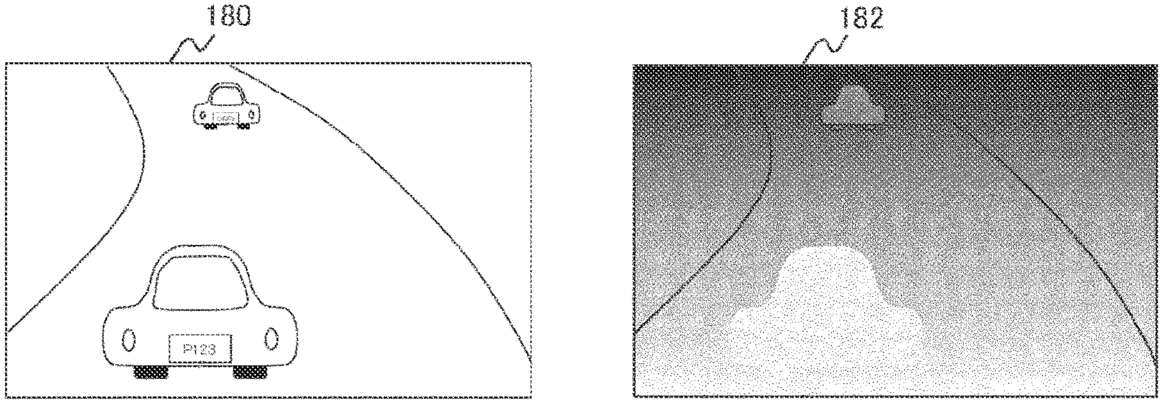
FIG. 17B
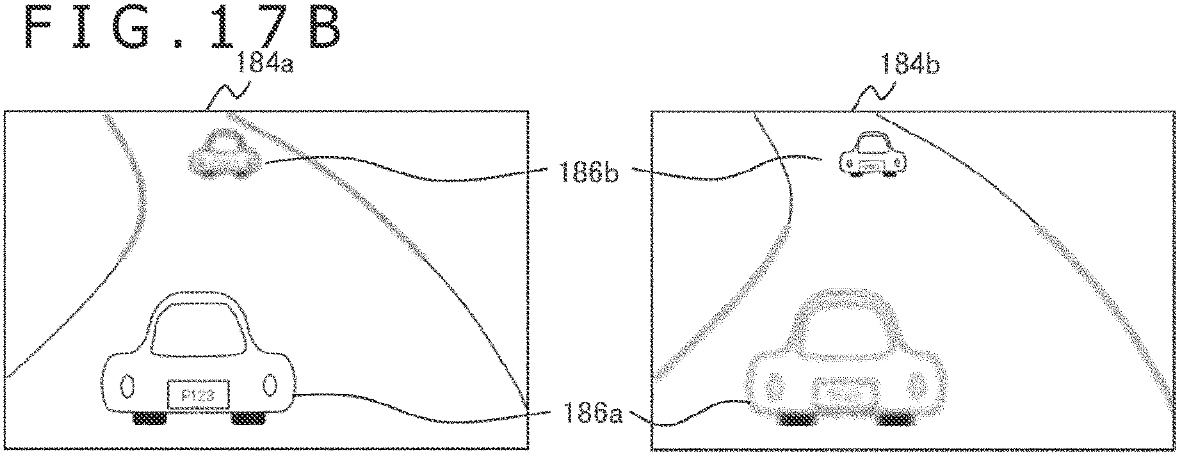

IMAGE DISPLAY SYSTEM AND IMAGE DISPLAY METHOD

CROSS REFERENCE TO RELATED APPLICATION

This application claims the benefit of Japanese Priority Patent Application JP 2022-091633 filed Jun. 6, 2022, the entire contents of which are incorporated herein by reference.

BACKGROUND

The present disclosure relates to an image display system and an image display method that display an image by projecting the image onto the retina.

A technology for projecting an image onto the human retina by using the Maxwellian view is being put into practical use in the field of wearable displays (refer to, for example, PCT Patent Publication No. WO2009/066465 (hereinafter, referred to as Patent Document 1)). In this technology, light representative of an image is converged at the center of the pupil of a user, and the image is formed on the retina in two-dimensional form. With this, the result of image formation is less likely to be affected by the crystalline lens, and an image can visually be recognized by users with substantially the same quality irrespective of personal visual acuity and the focus position, that is, a focus-free capability is easily obtained (refer to, for example, Mitsuru Sugawara and six other persons, "Every aspect of advanced retinal imaging laser eyewear: principle, free focus, resolution, laser safety, and medical welfare applications," SPIE OPTO, Feb. 22, 2018, Proceedings Volume 10545, MOEMS and Miniaturized Systems XVII, 105450O (hereinafter, referred to as Non-Patent Document 1)).

SUMMARY

According to Non-Patent Document 1, it has been known that the focus-free capability and visual resolution variously change depending on the state of a beam. For example, when the beam is adjusted in such a direction as to increase the visual resolution, the focus-free capability is degraded, which may possibly make it difficult for a user to view an image depending on his or her visual acuity. Conversely, when the beam is adjusted in such a direction as to enhance the focus-free capability, the visual resolution is relatively decreased. As described above, the resolution and the focus-free capability are in a trade-off relation. Therefore, it is difficult to balance between the resolution and the focus-free capability.

Further, when viewing an object in the real world, a person focuses on the object by changing the thickness of the crystalline lens according to the distance to the object. Meanwhile, when the above-described technology is used, the image to be visually recognized is less likely to be affected by the thickness of the crystalline lens. Therefore, even when the thickness of the crystalline lens physiologically changes according to the distance in the image, the appearance of the image remains unchanged, that is, a convergence-accommodation conflict occurs. Due to this, the sense of presence is likely to be degraded.

In view of the above circumstances, the present disclosure has been made, and it is desirable to provide a technology that allows a user to visually recognize a realistic image with increased quality during the use of a display technology for projecting an image onto the retina.

According to an embodiment of the present disclosure, there is provided an image display system including an eyeball state acquisition section, a beam control section, and an image projection section. The eyeball state acquisition section acquires information regarding a state of an eye of a user. The beam control section adjusts, according to the information regarding the state of the eye, a beam state of image laser light for forming pixels of a display image. The image projection section projects the image laser light onto a retina of the user.

According to another embodiment of the present disclosure, there is provided an image display method performed by an image display system. The image display method includes acquiring information regarding a state of an eye of a user, adjusting, according to the information regarding the state of the eye, a beam state of image laser light for forming pixels of a display image, and projecting the image laser light onto a retina of the user.

It should be noted that any combinations of the above-mentioned constituent elements and any conversions of expressions of the present disclosure between, for example, methods, devices, systems, computer programs, and recording media having computer programs recorded therein are also effective as the embodiments of the present disclosure.

According to the present disclosure, a realistic image can visually be recognized with increased quality during the use of a display technology for projecting an image onto the retina.

BRIEF DESCRIPTION OF THE DRAWINGS

FIG. 5 is a diagram illustrating configurations of functional blocks of a distance acquisition section, an eyeball state acquisition section, and a beam control section in the first embodiment;

FIG. 6 is a diagram illustrating how a computation block of the distance acquisition section acquires distances to a plurality of reflective surfaces in the first embodiment;

FIG. 7 is a diagram illustrating an example of the data structure of an unaided visual acuity table that is internally retained by an unaided visual acuity acquisition block in the first embodiment;

FIG. 15 is a diagram illustrating an example of the data structure of a resolution table that is internally retained by an image generation section in the second embodiment;

FIG. 16 is a diagram illustrating an example of the data structure of a beam state table that is internally retained by a beam state determination block in the second embodiment; and FIGS. 17A and 17B are schematic diagrams illustrating a display target image and a display resulting from a beam state adjustment in the second embodiment.

DETAILED DESCRIPTION OF THE PREFERRED EMBODIMENTS

First Embodiment

Figure 1:
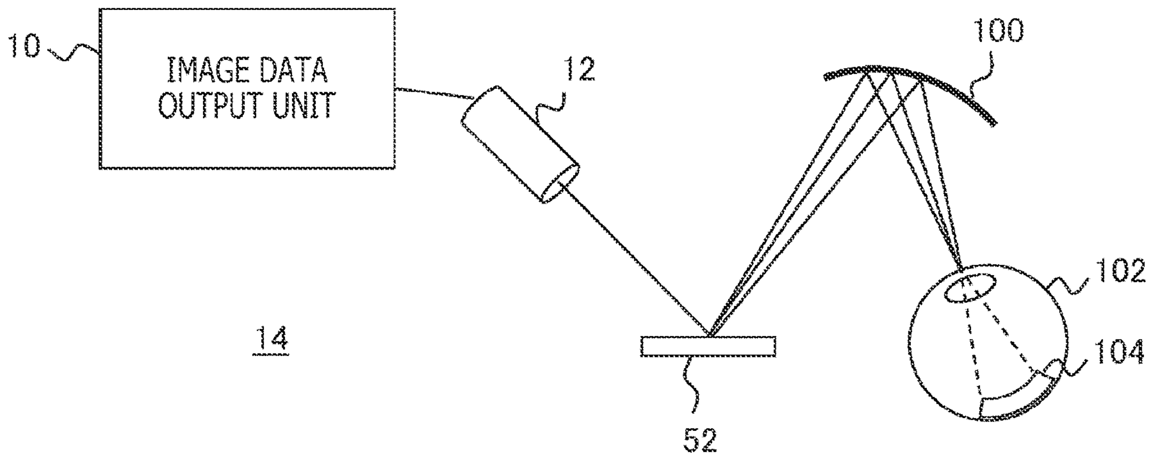
FIG. 1 is a diagram illustrating a basic exemplary configuration of an image display system to which a first embodiment of the present disclosure is applicable.

A first embodiment of the present disclosure relates to a display technology for projecting an image onto the retina of a user by using a laser beam scanning method. The laser beam scanning method is a method for forming an image on a target by performing a two-dimensional scan with laser light corresponding to pixels, with the use of a deflection mirror. FIG. 1 illustrates a basic exemplary configuration of an image display system to which the first embodiment is applicable. The image display system 14 depicted in the example of FIG. 1 includes an image data output unit 10, a light emission unit 12, a scanning mirror 52, and a reflective mirror 100.

The image data output unit 10 outputs data of a display target image to the light emission unit 12. The light emission unit 12 acquires the data and generates laser light indicating the colors of individual pixels forming the image. The laser light includes, for example, red (R), green (G), and blue (B) components. The scanning mirror 52 is controlled to change its angle around two axes and displaces, in two-dimensional directions, the destination of the laser light generated by the light emission unit 12. The light emission unit 12 sequentially changes the color of the laser light in synchronism with the oscillation of the scanning mirror 52. Thus, the image is formed with pixels colored at each specific time point.

The reflective mirror 100 receives the laser light reflected from the scanning mirror 52, and reflects the laser light toward an eyeball 102 of the user. The reflective mirror 100 is designed such that the laser light two-dimensionally scanned by the scanning mirror 52 is converged on the pupil of the eyeball 102 and is then two-dimensionally scanned over a retina 104. This increases the possibility of achieving a focus-free capability, which allows users to visually recognize an image with substantially the same quality at all times irrespective of unaided visual acuity and the focus position.

In practice, it is conceivable that the structure depicted in FIG. 1 may be fabricated in the form of a head-mounted display, smart glasses, or other wearable display worn over left and right eyes. Further, the example of FIG. 1 depicts a basic structure of a display system based on retinal direct drawing, but the present embodiment is not limited to such a structure. For example, a collimating lens or an additional mirror may be disposed in the path of laser light, or a control mechanism may be provided for each mirror.

The present embodiment improves the quality of a visually recognized image during the application of the display technology that uses the method depicted in FIG. 1. More specifically, the beam state of laser light is optimized for each of the users, and a finer image is thus visually recognized by the users. Disclosed in Non-Patent Document 1 is the influence of the state of laser light and the unaided visual acuity of an observer on an image projected onto the retina.

Figure 2:
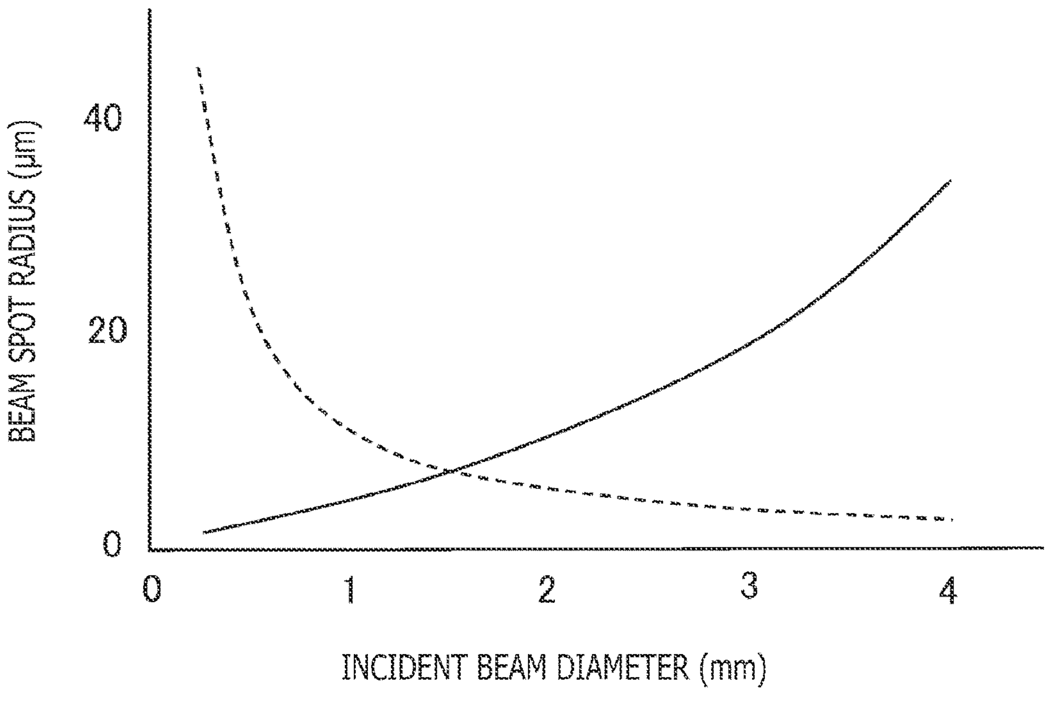
FIG. 2 illustrates a simulation result that is disclosed in Non-Patent Document 1 and that indicates the relation between the beam diameter of laser light incident on the eyeball and the radius of a beam spot on the retina.

FIG. 2 illustrates a simulation result that is disclosed in Non-Patent Document 1 and that indicates the relation between the beam diameter of laser light incident on the eyeball and the radius of a beam spot on the retina. The solid line indicates the result of calculation that is performed on the basis of geometrical optics in consideration of chromatic aberration. The dotted line indicates the result of calculation that is performed in consideration of light diffraction. In terms of geometrical optics, the beam spot on the retina becomes smaller with a decrease in an incident beam diameter. However, according to the diffraction phenomenon, the beam spot on the retina becomes smaller with an increase in the incident beam diameter.

In other words, there exists an incident beam diameter that gives a local minimum to the beam spot on the retina. In order to increase resolution when an image displayed by retinal direct drawing is visually recognized, it is preferable that the incident beam diameter be adjusted for the local minimum. In the example of FIG. 2, it is conceivable that the incident beam diameter may be set to 1.5 mm. However, the indicated result is obtained under specific conditions. The optimal incident beam diameter varies with a user's unaided visual acuity and a beam divergence angle.

Figure 3B:
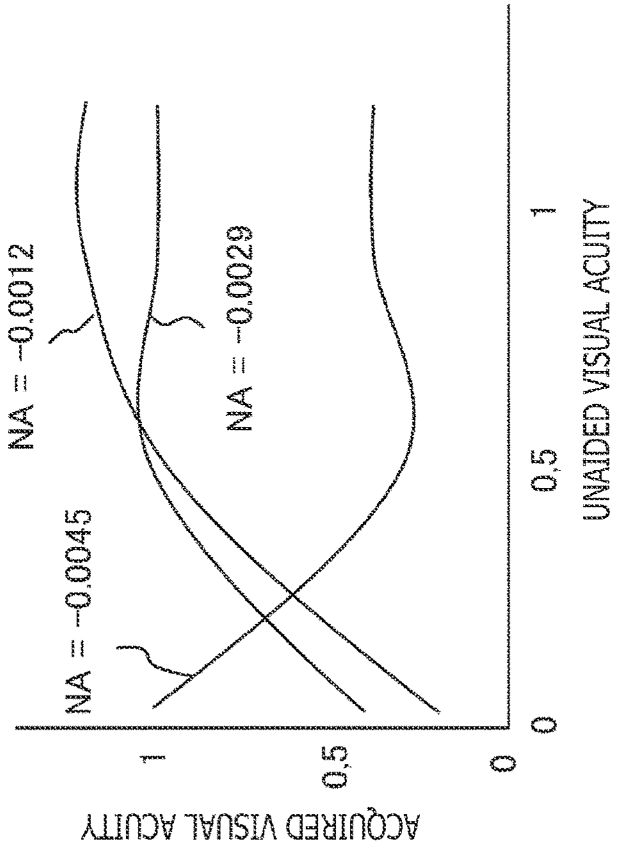
FIGS. 3A and 3B are diagrams illustrating experiment results that are disclosed in Non-Patent Document 1 and that indicate the relation between acquired visual acuity and unaided visual acuity.
Figure 3A:
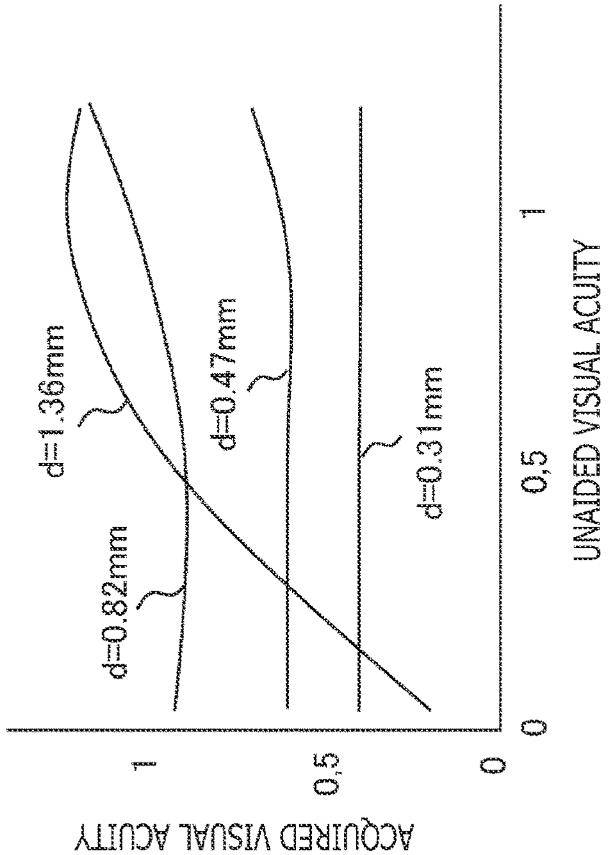

FIGS. 3A and 3B illustrate experiment results that are disclosed in Non-Patent Document 1 and that indicate the relation between acquired visual acuity and unaided visual acuity. The acquired visual acuity herein is visual acuity of a user who is visually recognizing an image projected onto the retina of the user. FIG. 3A depicts changes in the acquired visual acuity with respect to the unaided visual acuity in a situation where the beam is parallel light and where an incident beam diameter d is varied in order of 0.31, 0.47, 0.82, and 1.36 mm. FIG. 3B depicts changes in the acquired visual acuity with respect to the unaided visual acuity in a situation where the beam diameter is 1.49 mm and where a numerical aperture NA is varied from −0.0012 through −0.0029 to −0.0045. It should be noted that the numerical aperture NA is defined by the following equation where θ represents a half-angle (divergence angle) of the incident beam.

$$NA=\sin\theta$$

As seen from FIG. 3A, in a case where the beam is parallel light and where the beam diameter is between 0.31 and 0.82 mm, the acquired visual acuity is not significantly dependent on the unaided visual acuity, that is, the focus-free capability is obtained. Particularly, when the beam diameter d is 0.82 mm, the acquired visual acuity reaches its highest level. On the other hand, when the beam diameter d is 1.36 mm, the acquired visual acuity significantly varies with the unaided visual acuity. For example, when the unaided visual acuity is approximately one, the highest acquired visual acuity is obtained. In contrast, when the unaided visual acuity is 0.1, the acquired visual acuity is lower than that in the case of the other beam diameters. That is, it is obvious that the appropriate beam diameter varies with the user's unaided visual acuity in a situation where an image is to be viewed with the finest resolution possible.

Meanwhile, when the numerical aperture is −0.0012 or −0.0029 as indicated in FIG. 3B with the beam diameter fixed at 1.49 mm, a similar result to the case of FIG. 3A where the beam is parallel light and where the beam diameter is 1.36 mm is obtained. That is, when the unaided visual acuity is approximately 0.5 or lower, the acquired visual acuity decreases with a decrease in the unaided visual acuity. However, in a case where the numerical aperture is −0.0045, the acquired visual acuity exhibits an opposite behavior. More specifically, when the unaided visual acuity is approximately 0.5 or lower, the acquired visual acuity increases with a decrease in the unaided visual acuity. Further, when the unaided visual acuity is approximately one, the acquired visual acuity is significantly lower than that in the case of different numerical apertures. In other words, it is obvious that, in a situation where an image is to be viewed with the finest resolution possible, the appropriate numerical aperture and hence the beam divergence angle diameter vary with the user's unaided visual acuity.

Moreover, as can be seen from the above-described results, as the fineness (resolution) of a visually recognized image is increased, the focus-free capability is more impaired. This phenomenon theoretically occurs because the conditions for the optimal beam diameter and the beam divergence angle vary in relation to to the refractive power of a user's eye. In the present embodiment, the beam state is automatically adjusted according to the state of the eyes of each of the users, so that the users can view highly fine images with higher resolution. Since anyone can view such a fine image, the focus-free capability is also achieved.

Figure 4:
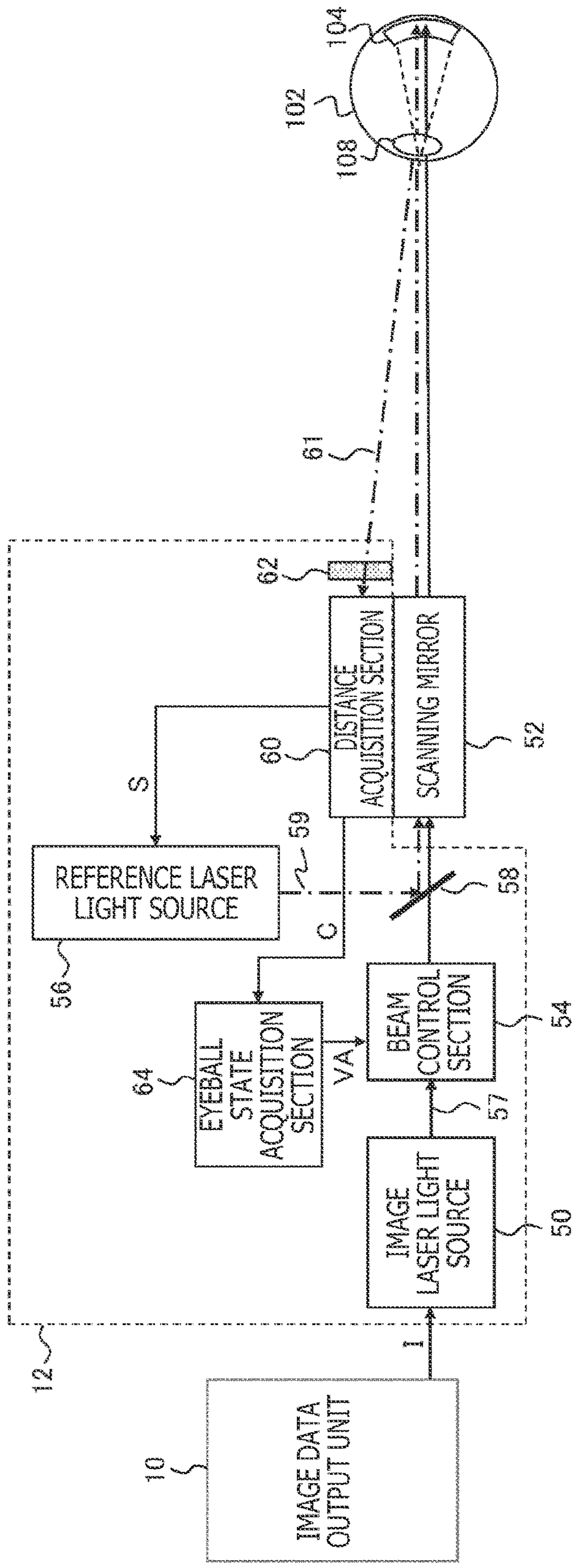
FIG. 4 is a diagram illustrating a detailed configuration of the image display system according to the first embodiment.

FIG. 4 illustrates a detailed configuration of the image display system according to the present embodiment. As mentioned earlier, the image display system 14 includes the image data output unit 10, the light emission unit 12, and the scanning mirror 52. It should be noted that the reflective mirror 100 is not depicted in FIG. 4. The light emission unit 12 includes an image laser light source 50 and a beam control section 54 as an image projection section for emitting, to the retina 104, light that forms pixels of a projection image to be projected onto the retina 104. The image laser light source 50 generates image laser light 57 on the basis of image data I outputted from the image data output unit 10. The image laser light 57 indicates the colors of the individual pixels of the projection image.

The image laser light 57 includes, for example, three different laser light waves corresponding to R, G, and B. However, the wavelength and the number of waves are not limited to particular ones as long as they indicate the colors corresponding to pixel values. The beam control section 54 adjusts at least either the beam diameter or divergence angle of the image laser light 57 according to the state of the user's eye. Hereinafter, both the beam diameter and the convergence angle or either one of them may generically be referred to as the "beam state." An example of specific means for adjusting the beam state will be described later. The adjusted image laser light 57 is reflected from the scanning mirror 52 and finally enters the eyeball 102 of the user.

For example, a microelectromechanical systems (MEMS) mirror is employed as the scanning mirror 52. The MEMS mirror is a small-size, low-power-consumption device that is able to accurately control angular changes around two axes by being electromagnetically driven. However, the method for driving the scanning mirror 52 is not limited to a particular one. The scanning mirror 52 includes a control mechanism for controlling its angle in synchronism with the colors of the image laser light 57, which forms the pixels of the projection image. The control mechanism may alternatively be included in the image data output unit 10.

In the present embodiment, the light emission unit 12 further has a function of acquiring information regarding the state of the eyeball 102 of the user. More specifically, the light emission unit 12 acquires predetermined parameters which are related to the structure of the eyeball 102 and which can be used to estimate the unaided visual acuity. Examples of the predetermined parameter include the thickness of a crystalline lens 108 and the length of the eyeball in the depth direction (eye axial length). The light emission unit 12 estimates the unaided visual acuity of the user on the basis of such visual acuity estimation parameters, and emits the image laser light 57 in the optimal beam state, which varies from one user to another.

Specifically, the light emission unit 12 includes a reference laser light source 56, a beam splitter 58, a reference laser light transmission filter 62, a distance acquisition section 60, and an eyeball state acquisition section 64. The reference laser light source 56 outputs reference laser light for acquiring the visual acuity estimation parameters. The beam splitter 58 superimposes the reference laser light on the image laser light and introduces the resulting laser light to the scanning mirror 52. The reference laser light transmission filter 62 transmits therethrough light having the wavelength of the reference laser light. The distance acquisition section 60 detects the reflected reference laser light and acquires the distance to the point where the reference laser light is reflected. The eyeball state acquisition section 64 acquires the visual acuity estimation parameters from information regarding the acquired distance and estimates the unaided visual acuity.

In the above example, the reference laser light source 56 and the beam splitter 58 function as a reference light emission section. As reference laser light 59, the reference laser light source 56 generates, for example, near-infrared laser light having a pulse width of 100 picoseconds to several nanoseconds. The beam splitter 58 is disposed in such a manner as to make the reference laser light 59 join the path of the image laser light 57 and to introduce the reference laser light 59 to the scanning mirror 52. With such a beam splitter 58, the reference laser light 59 is, in a common path shared by the image laser light 57, reflected from the scanning mirror 52 and delivered to the eyeball 102, for example, through a reflective mirror. It should be noted that, when paths are substantially common to each other, they may be regarded as the "common path" even though they are slightly displaced from each other.

The distance acquisition section 60 detects the reference laser light 59 reflected from tissues in the eyeball 102, and thus acquires the distance to the point where the reference laser light is reflected. Part of the reference laser light 59 delivered to the pupil of the eyeball 102 is transmitted through various tissues in the eyeball and delivered to the retina 104, while the other reference laser light 59 is reflected from the surfaces of the tissues. For example, part of the reference laser light 59 is reflected from a surface (front surface) of the crystalline lens 108 facing the pupil, and the remaining reference laser light 59 is transmitted through the front surface of the crystalline lens 108. Part of the transmitted laser light is reflected from a surface (back surface) of the crystalline lens 108 facing the retina, and the remaining transmitted laser light is transmitted through the back surface of the crystalline lens 108. The last remaining laser light is delivered to and reflected from the retina 104.

The distance acquisition section 60 detects, at light-receiving elements thereof, photons that are reflected from a plurality of surfaces in the above-described manner, and derives the distance to each surface on the basis of the time lag between the emission and detection of the reference laser light 59. The distance acquisition section 60 includes, for example, a direct time-of-flight (dToF) sensor and is driven in synchronism with the emission of the reference laser light 59. More specifically, in response to a synchronization signal S inputted from the distance acquisition section 60, the reference laser light source 56 periodically generates a pulse of the reference laser light 59. The distance acquisition section 60 repeatedly measures, for a predetermined period of time, the time lag between a time point when the reference laser light 59 is emitted, which is based on the time point when the synchronization signal S is outputted, and a time point when reflected light 61 of the reference laser light 59 is detected.

When the time lag between the emission of the reference laser light 59 and the detection of the reflected light 61 is Δt and the speed of light is c, a distance C between the light-receiving element of the distance acquisition section 60 and the reflective surface is theoretically determined by the following equation.

$$C = c \times \Delta t / 2$$

It should be noted that a port through which the laser light is emitted from the scanning mirror 52 is substantially the same as the light-receiving surface of the distance acquisition section 60. In the present embodiment, however, the method of measuring the distance to the point of reflection by detecting the reflection of the reference laser light is not limited to dToF.

In the present embodiment described above, there are a plurality of reflective surfaces from which the reference laser light is reflected. Therefore, the number of photons detected by the distance acquisition section 60 takes a local maximum at a plurality of time points t1, t2, t3, which correspond to the distances to the reflective surfaces. For example, the distance acquisition section 60 accumulates and counts temporal changes in the number of detected photons from the time point when the laser light is emitted, and thus acquires the time lags Δt1, Δt2, Δt3, . . . that cause the number of photons to take the local maximum. As a result, distances C1, C2, C3, . . . to the plurality of reflective surfaces can be determined highly accurately on the basis of the above equation.

It should be noted that, although the path of the reference laser light 59 is linear in FIG. 4, calculations are performed in a similar manner even if the path of the laser light is nonlinear as depicted in FIG. 1. In such a case, the "distance" may be regarded as the path length of the laser light. In any case, when the reference laser light 59 is emitted along the same path as the image laser light 57, the present embodiment ensures that the laser light reaches the crystalline lens 108 and the retina 104 under conditions where the user is able to view an image.

The eyeball state acquisition section 64 acquires, from the distance acquisition section 60, a data set C including the distances C1, C2, C3, . . . to the plurality of reflective surfaces, and acquires the visual acuity estimation parameters by using the acquired data set C. For example, the eyeball state acquisition section 64 acquires, as the thickness of the crystalline lens 108, the difference between the distance to the front surface of the crystalline lens 108 and the distance to the back surface of the crystalline lens 108. The eyeball state acquisition section 64 estimates unaided visual acuity VA of the user on the basis of the acquired thickness, and reports the estimated unaided visual acuity VA to the beam control section 54.

The beam control section 54 adjusts the image laser light 57 until the beam state becomes suitable for the reported unaided visual acuity VA. It should be noted that unaided acuity acquisition by the reference laser light source 56, the distance acquisition section 60, and the eyeball state acquisition section 64 may be performed only once as an initial operation when the user begins to view images such as content by using the image display system according to the present embodiment.

Alternatively, the above-mentioned unaided acuity acquisition may be performed while the user is viewing images, at regular intervals or at a predetermined timing such as a timing when a scene changes. In the present embodiment, image display processing and visual acuity estimation processing do not interfere with each other and are compatible with each other within the same system. Hence, the user is able to enjoy viewing images under optimal conditions without having trouble.

FIG. 5 illustrates configurations of functional blocks of the distance acquisition section 60, the eyeball state acquisition section 64, and the beam control section 54 in the present embodiment. The functional blocks depicted in FIG. 5 can be implemented by hardware such as various sensors and microprocessors or implemented by software such as programs for performing a data input/output function, a computation function, a communication function, and various other functions. Hence, it will be understood by persons skilled in the art that the functional blocks may variously be implemented by hardware only, by software only, or by a combination of hardware and software. The method of implementing the functional blocks is not limited to a particular one.

Further, the distance acquisition section 60, the eyeball state acquisition section 64, and the beam control section 54 may be implemented as one or two devices or as four or more devices in practice. Moreover, some of the depicted functions of the distance acquisition section 60 and the beam control section 54 may be included in the eyeball state acquisition section 64. Alternatively, some or all of the functions of the eyeball state acquisition section 64 may be included in the distance acquisition section 60 or in the beam control section 54.

The distance acquisition section 60 includes a synchronization signal output block 72, a detection block 70, and a computation block 74. The synchronization signal output block 72 outputs a synchronization signal to the reference laser light source 56. The detection block 70 detects the reflected reference laser light. The computation block 74 acquires the distance to a reflection position according to the result of the detection. The synchronization signal output block 72 generates the synchronization signal for starting the generation of the pulse of the reference laser light, as mentioned above, and gives the generated synchronization signal to the reference laser light source 56. The detection block 70 includes an array of light-receiving elements, detects the reflected reference laser light when the eyeball is hit by the pulse of the reference laser light generated by the reference laser light source 56 in response to the synchronization signal, and reports temporal changes in the number of detections to the computation block 74.

The computation block 74 determines the time point when the pulse of the reference laser light is emitted, according to the timing of the synchronization signal generated by the synchronization signal output block 72. Then, as mentioned earlier, the computation block 74 accumulates and counts the number of times the reflected light is detected, for a plurality of pulses, in relation to the elapsed time from the time point of the emission, and thus determines the plurality of time lags Δt1, Δt2, Δt3, . . . that give the local maximum to the number of detections. Further, the computation block 74 uses the above equation to derive distance values that correspond to the respective determined time lags.

The eyeball state acquisition section 64 includes an unaided visual acuity acquisition block 78 that estimates the unaided visual acuity of the user by using the derived distance values. More specifically, the unaided visual acuity acquisition block 78 determines one or more unaided visual acuity estimation parameters such as the crystalline lens thickness and the eye axial length according to the difference between the distance values. Then, the eyeball state acquisition section 64 estimates the unaided visual acuity of the user according to the values of the determined unaided visual acuity estimation parameters. For the purpose of estimating the unaided visual acuity, the unaided visual acuity acquisition block 78 has an unaided visual acuity table retained in an internal memory thereof, for example. The unaided visual acuity table defines the association between the unaided visual acuity estimation parameters and the unaided visual acuity.

The beam control section 54 includes a beam state determination block 80 and an adjustment block 82. The beam state determination block 80 determines the optimal value of the beam state. The adjustment block 82 adjusts the beam state of the image laser light according to the result of the determination. The beam state determination block 80 acquires an estimated value of the user's unaided visual acuity from the eyeball state acquisition section 64, and determines the beam state optimal for the user's unaided visual acuity. For the purpose of determining the beam state, the beam state determination block 80 has a beam state table retained in an internal memory thereof, for example. The beam state table defines the association between the unaided visual acuity and the optimal beam state.

The adjustment block 82 adjusts the image laser light to obtain the beam state determined by the beam state determination block 80. For the purpose of adjusting the image laser light, the adjustment block 82 includes means for adjusting at least either the beam diameter or the beam divergence angle. For example, the adjustment block 82 includes a beam expander for use in adjusting the beam diameter.

The beam expander is a well-known device that includes a first lens for expanding the diameter of incident laser light and a second lens for turning such expanded laser light into parallel light and that is able to change the magnification of the beam diameter by adjusting the distance between the first and second lenses (refer to, for example, "beam expander," [online], Edmund Optics Japan, [search on May 9, 2022], Internet <URL: https://www.edmundoptics.jp/knowledge-center/application-notes/lasers/beam-expanders>). However, the means for adjusting the beam diameter is not limited to the beam expander.

Further, the adjustment block 82 includes, for example, a device that is used for adjusting the beam divergence angle and that is equipped with any of a diffusion lens, a condenser lens, a liquid lens, and photonic crystals. When the diffusion lens or the condenser lens is used, the divergence angle can be adjusted by shifting the lens position in the axial direction. In this instance, the adjustment block 82 needs to mechanically move the lens by using an actuator, and the time required for the adjustment is approximately 100 msec to 1 sec.

The liquid lens is a device that changes the refractive index of incident light by inducing interface deformation by changing a voltage applied into a holder in which water or other polar liquid and silicone oil or other nonpolar liquid are enclosed (refer to, for example, Japanese Patent Laid-open No. 2011-90054). When provided with a device equipped with the liquid lens, the adjustment block 82 is able to control the divergence angle simply by changing the applied voltage, and thus significantly increase the response speed for the adjustment.

A device equipped with the photonic crystals uses the combination of a photonic crystal with a fixed period of refractive index profile and a photonic crystal with a continuously varying period of refractive index profile, changes the difference between the above-mentioned periods by shifting the position of an electrode to be driven, and thus adjusts a beam emission angle (refer to, for example, Japanese Patent Laid-open No. 2013-211542). When provided with the device equipped with the photonic crystals, the adjustment block 82 is also able to control the divergence angle simply by changing the electrode to be driven. It should be noted that the means for adjusting the beam state in the present embodiment is not limited to the above-described one.

FIG. 6 is a diagram illustrating how the computation block 74 of the distance acquisition section 60 acquires the distances to the plurality of reflective surfaces. As mentioned earlier, part of the reference laser light is reflected from the front and back surfaces of the crystalline lens, and the remaining reference laser light is delivered to the retina. Therefore, in the distance acquisition section 60, photons corresponding in number to reflectance are detected multiple times with a time tag each time a reference laser pulse is emitted. The histogram in FIG. 6 schematically depicts changes in the number of photon detections in relation to the elapsed time from a time point when the reference laser pulse is emitted, and indicates that three local maxima are obtained.

The local maxima can be obtained more clearly by increasing the number of reference laser pulse emissions and adding the results of detection to the histogram. The time lags Δt1, Δt2, Δt3 giving the local maxima correspond to the distances C1, C2, C3 to the surfaces causing the relevant reflections. For ease of understanding, FIG. 6 assumes that the reflections are caused by the front and back surfaces of the crystalline lens and by the retina. More specifically, the distance from the light-receiving surface of the detection block 70 to the front surface of the crystalline lens is C1, the distance to the back surface of the crystalline lens is C2, and the distance to the retina is C3. Even if any other reflective surfaces are present, the local maxima indicative of the respective surfaces of the crystalline lens and the retina can be identified according to the positional relation between the reflective surfaces when the structure of the eyeball is taken into consideration.

The unaided visual acuity acquisition block 78 acquires data regarding a plurality of distance values obtained in the above manner, and determines, for example, the distance difference between the back and front surfaces of the crystalline lens, i.e., C2−C1, as the thickness of the crystalline lens. Alternatively, the unaided visual acuity acquisition block 78 determines the distance difference between the retina and the front surface of the crystalline lens, i.e., C3–C1, as the eye axial length. It should be noted that the type and number of the unaided visual acuity estimation parameters are not limited to particular ones as long as the unaided visual acuity can be estimated on the basis of the distances to the reflective surfaces of the eyeball. Further, it is sufficient if the crystalline lens thickness and the eye axial length are indices for deriving the unaided visual acuity, and they may not be exact numerical values based on the general definition.

FIG. 7 illustrates an example of the data structure of the unaided visual acuity table that is internally retained by the unaided visual acuity acquisition block 78. In the example depicted in FIG. 7, an unaided visual acuity table 110 includes data indicating the association between the crystalline lens thickness and the unaided visual acuity. It has been known that the unaided visual acuity depends on the crystalline lens thickness (refractive error). More specifically, when the crystalline lens thickness is greater than a normal value, the refractive index increases, causing near-sightedness which is a condition where incident light forms an image in front of the retina. On the other hand, when the crystalline lens thickness is smaller than the normal value, the refractive index decreases, causing far-sightedness which is a condition where the incident light forms an image behind the retina.

Hence, when the unaided visual acuity table 110 depicted in FIG. 7 has been created on the basis of, for example, experiments or theoretical calculations, the unaided visual acuity acquisition block 78 is able to estimate the unaided visual acuity from the actually determined crystalline lens thickness. It should be noted that numerical values depicted in FIG. 7 are merely examples, and the numerical values may be set with finer granularity. Further, as long as the unaided visual acuity can be derived from the crystalline lens thickness, the data used for the derivation is not limited to a table and may alternatively be, for example, a calculation formula.

Meanwhile, it has been known that the unaided visual acuity also depends on the eye axial length (axial error). More specifically, when the eye axial length is greater than a normal value, the near-sightedness, which is the condition where incident light forms an image in front of the retina, occurs. On the other hand, when the eye axial length is smaller than the normal value, the far-sightedness, which is the condition where incident light forms an image behind the retina, occurs. Hence, the unaided visual acuity table may include data indicating the association between the eye axial length and the unaided visual acuity. Alternatively, the unaided visual acuity table may include data indicating the association between the unaided visual acuity and the combination of the crystalline lens thickness and the eye axial length or include data indicating the association between the unaided visual acuity and any other parameter.

Figures 8, 9:
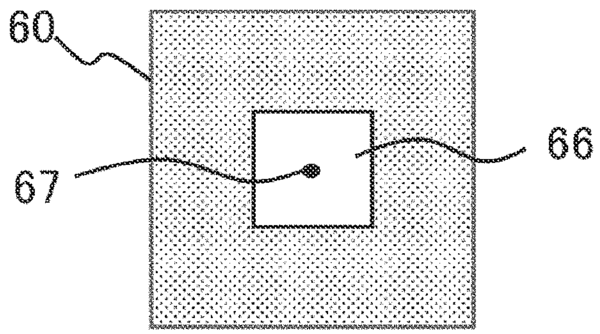
FIG. 8 is a diagram illustrating an example of the data structure of a beam state table that is internally retained by a beam state determination block in the first embodiment.
FIG. 9 is a diagram illustrating an example of the shape of a light-receiving surface of the distance acquisition section in the first embodiment.

FIG. 8 illustrates an example of the data structure of the beam state table that is internally retained by the beam state determination block 80. In the example depicted in FIG. 8, a beam state table 112 includes data indicating the association between the unaided visual acuity and the beam state suitable for the unaided visual acuity. As the beam state, the depicted example indicates the beam diameter and the numerical aperture corresponding to the divergence angle. Alternatively, however, only one of them may be indicated as the beam state.

In a case where only the beam diameter is to be adjusted, as depicted in FIG. 3A, the divergence angle is first fixed at a specified value. Then, experiments or calculations are performed to determine such a beam diameter as to enable each level of unaided visual acuity to obtain the highest acquired visual acuity, and the association between the unaided visual acuity and the beam diameter is defined. In a case where only the divergence angle is to be adjusted, as depicted in FIG. 3B, the beam diameter is first fixed at a specified value. Then, experiments or calculations are performed to determine such a divergence angle (numerical aperture) as to enable each level of unaided visual acuity to obtain the highest acquired visual acuity, and the association between the unaided visual acuity and the divergence angle is defined. Further, in a case where both the beam diameter and the divergence angle are to be adjusted, both of them are regarded as variables. Then, experiments or calculations are performed to determine the combination of the beam diameter and the divergence angle in such a manner that each level of unaided visual acuity can obtain the highest acquired visual acuity, and the association between the beam diameter and the divergence angle is defined.

The beam state determination block 80 references the beam state table 112 to determine the optimal beam state according to the user's unaided visual acuity obtained by the unaided visual acuity acquisition block 78 of the eyeball state acquisition section 64, and reports the determined optimal beam state to the adjustment block 82. It should be noted that numerical values depicted in FIG. 8 are merely examples, and the numerical values may be set with finer granularity. Further, as long as the optimal value of the beam state can be derived from the unaided visual acuity, the data to be used for such derivation is not limited to a table and may alternatively be, for example, a calculation formula.

FIG. 9 illustrates an example of the shape of the light-receiving surface of the distance acquisition section 60 in the present embodiment. That is, FIG. 9 presents a front view of the distance acquisition section 60 as viewed from the reference laser light transmission filter 62 in the configuration depicted in FIG. 4. As depicted in FIG. 9, the distance acquisition section 60 has such a structure that light-receiving elements are arrayed on a hollowed rectangular surface having an opening 66 at the center thereof. Needless to say, the reference laser light transmission filter 62 is similar in shape to the distance acquisition section 60. The opening 66 forms a port through which the image laser light 57 and the reference laser light 59 reflected from the scanning mirror 52 are emitted.

That is, the distance acquisition section 60 detects the reflected reference laser light at a position circumscribing the port through which the above-mentioned laser light is emitted. As long as the reflected reference laser light is detected, the shape of the opening 66 or the surface on which the light-receiving elements are arrayed is not limited to a particular shape. In the present embodiment, the laser beam scanning method is adopted to sequentially irradiate individual pixels with laser light. Hence, even when the light-receiving surface of the distance acquisition section is positioned to circumscribe the laser light emitting port as depicted in FIG. 9, distance acquisition and image display do not interfere with each other.

Further, as depicted in FIG. 9, when the light-receiving surface for receiving the reflected light is positioned to enclose the opening 66, which is the laser light emitting port, the laser light emission axis can be aligned with a central axis 67 of the light-receiving surface (the vertical axis passing through the center of the light-receiving surface). As a result, with the use of a mechanism for displaying an image, information regarding the state of the eyeball can be acquired effortlessly and accurately. It should be noted that it is sufficient if the spacing interval between the light-receiving element array on the distance acquisition section 60 and the laser light emitting port is within such a very short distance range that the light-receiving element array and the laser light emitting port are considered to be in contact with each other.

Figure 10:
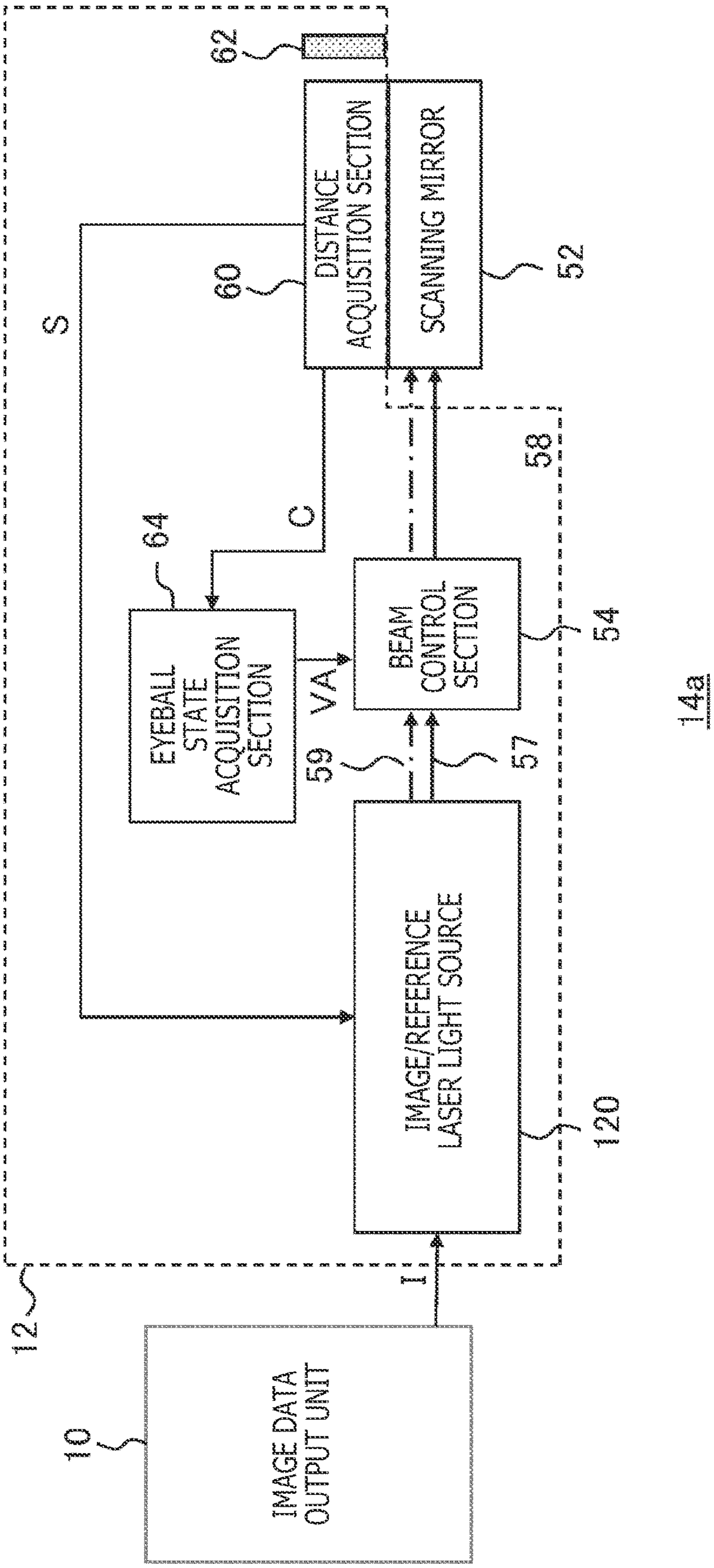
FIG. 10 is a diagram illustrating another example of the configuration of the image display system according to the first embodiment.

FIG. 10 illustrates another example of the configuration of the image display system according to the present embodiment. In FIG. 10, constituent elements similar to the constituent elements of the image display system 14 depicted in FIG. 4 are denoted by the same reference signs. More specifically, an image display system 14*a* depicted in FIG. 10 includes the image data output unit 10, the beam control section 54, the eyeball state acquisition section 64, the distance acquisition section 60, the scanning mirror 52, and the reference laser light transmission filter 62, which are depicted in FIG. 4. However, in the example of FIG. 10, an image/reference laser light source 120 is provided in place of the image laser light source 50 and the reference laser light source 56. The image/reference laser light source 120 is a laser module for generating image projection laser light and reference laser light from positions in the same plane that are close to each other.

The image/reference laser light source 120 not only generates the image laser light on the basis of the image data I acquired from the image data output unit 10, but also generates the pulse of the reference laser light according to the synchronization signal S from the distance acquisition section 60. The other operations of the image/reference laser light source 120 may be similar to the operations depicted in FIG. 4. According to the above-described configuration, the image display system can be downsized as compared with the configuration depicted in FIG. 4. Further, the laser light generated from the image/reference laser light source 120 need not be transmitted through the beam splitter and thus can be delivered to the target without affecting laser light intensity. This reduces the power consumption.

According to the present embodiment described above, in the image display system which projects an image onto the retina by using the laser beam scanning method, the reference laser light is emitted to the eyeball with the use of an image laser light emission mechanism, and the reflected reference laser light is detected, thereby acquiring the state of the eyeball. More specifically, the image display system estimates the unaided visual acuity of the user by acquiring the predetermined parameters affecting the unaided visual acuity. Subsequently, the image display system optimizes the beam state of the image laser light, and thus enables the user to visually recognize a fine image with the highest resolution possible irrespective of the user's unaided visual acuity.

Further, since the mechanism for displaying an image is used to emit the reference laser light to the eyeball, it is not necessary to use a special device for measuring visual acuity. That is, measurements can be made automatically while the user wears, for example, a wearable display for viewing images, and the results of measurements can immediately be reflected in the beam state. Consequently, accurate adjustments can be made without the user knowing. Moreover, since the reference laser light is emitted along the same path as the image laser light, the eyeball can accurately be measured without the trouble of performing calibration, for example.

Second Embodiment

In the first embodiment, the beam state is adjusted to ensure visual recognition of images with the highest resolution possible, without regard to the unaided visual acuity. However, in a second embodiment, the resolution of an image to be visually recognized is changed to match changes in a biological focal distance. More specifically, in the second embodiment, the distance in which the user focuses on something is estimated on the basis of the crystalline lens thickness, and the beam state is adjusted on a real time basis according to the estimated distance.

Figures 11A, 11B:
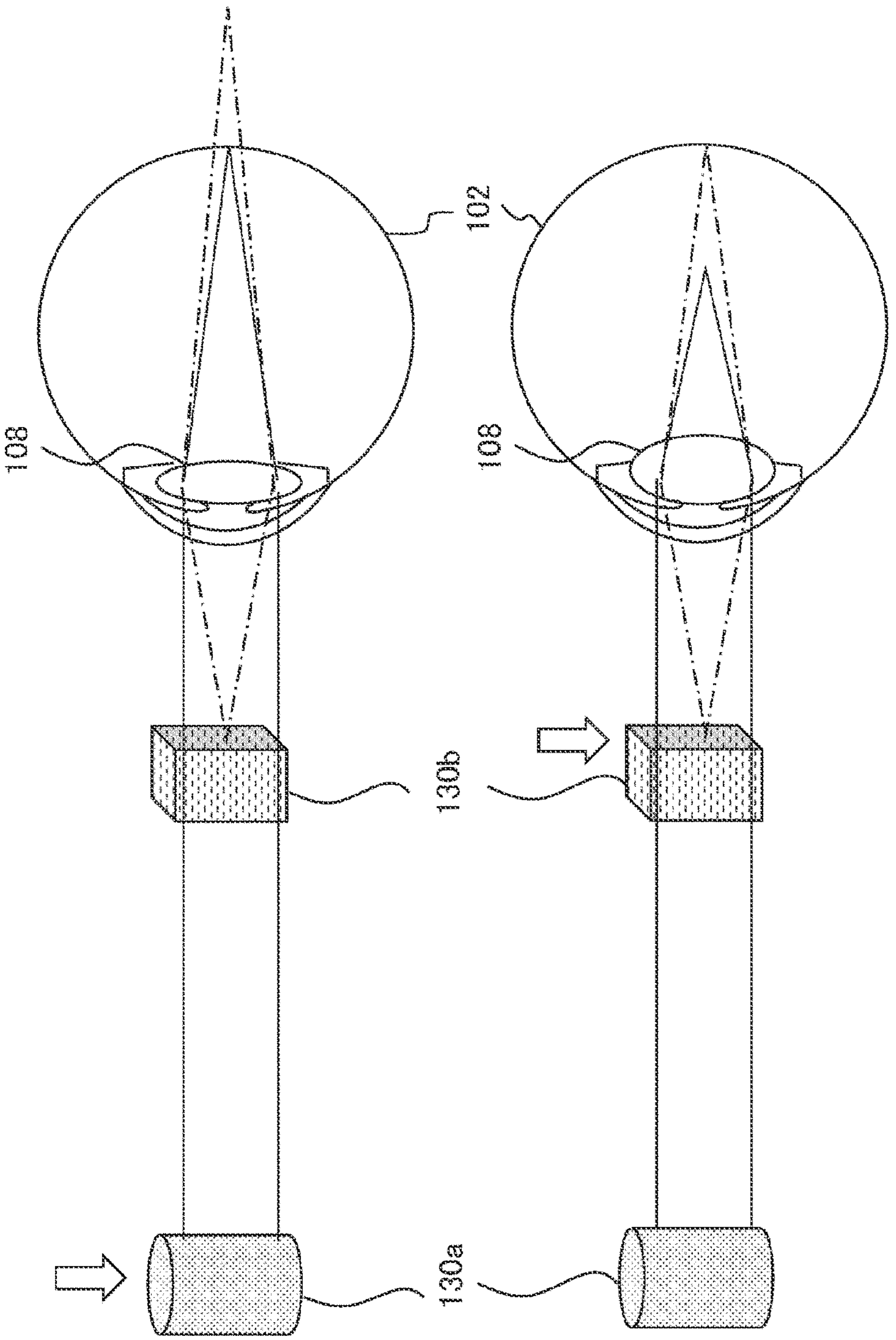
FIGS. 11A and 11B are diagrams illustrating the relation between the focal distance and the crystalline lens thickness, the relation being used in a second embodiment of the present disclosure.

FIGS. 11A and 11B are diagrams illustrating the relation between the focal distance and the crystalline lens thickness. FIGS. 11A and 11B are for comparing the states of the eyeball 102 in different situations where the user focuses on one of two objects 130*a* and 130*b* that are positioned at different distances. Here, the object on which the user focuses is indicated by an arrow. When the user views (focuses on) the distant object 130*a* as depicted in FIG. 11A, the crystalline lens 108 of the eyeball 102 becomes thin. Consequently, as indicated by the solid line, the image of the currently viewed object 130*a* is formed on the retina and recognized as a clear image. In this case, however, the image of the nearby object 130*b* looks blurry because it is formed behind the retina as indicated by the dashed-dotted line.

When the user views (focuses on) the nearby object 130*b* as depicted in FIG. 11B, the crystalline lens 108 of the eyeball 102 becomes thick. Consequently, as indicated by the dashed-dotted line, the image of the currently viewed object 130*b* is formed on the retina and recognized as a clear image. In this case, however, the image of the distant object 130*a* looks blurry because it is formed in front of the retina as indicated by the solid line.

When a display technology based on retinal direct drawing is adopted, as mentioned earlier, images are visually recognized in the same state no matter where the user's focus is. In other words, even when the user focuses on the image of an object, the user feels that the image is out of focus, that is, a convergence-accommodation conflict occurs. In the present embodiment, the crystalline lens thickness is acquired in parallel with image display, and then, the focal distance is estimated on a real time basis according to the acquired crystalline lens thickness. Subsequently, in the three-dimensional space of the display target, that is, in a virtual space of or the space of a live captured image of the display target, the image of an object placed at a position corresponding to the focal distance is visually recognized with high resolution, and the image of an object placed at a distant position not corresponding to the focal distance is visually recognized with low resolution. In this manner, the convergence-accommodation conflict is resolved, and a more realistic image representation is achieved.

Figure 12:
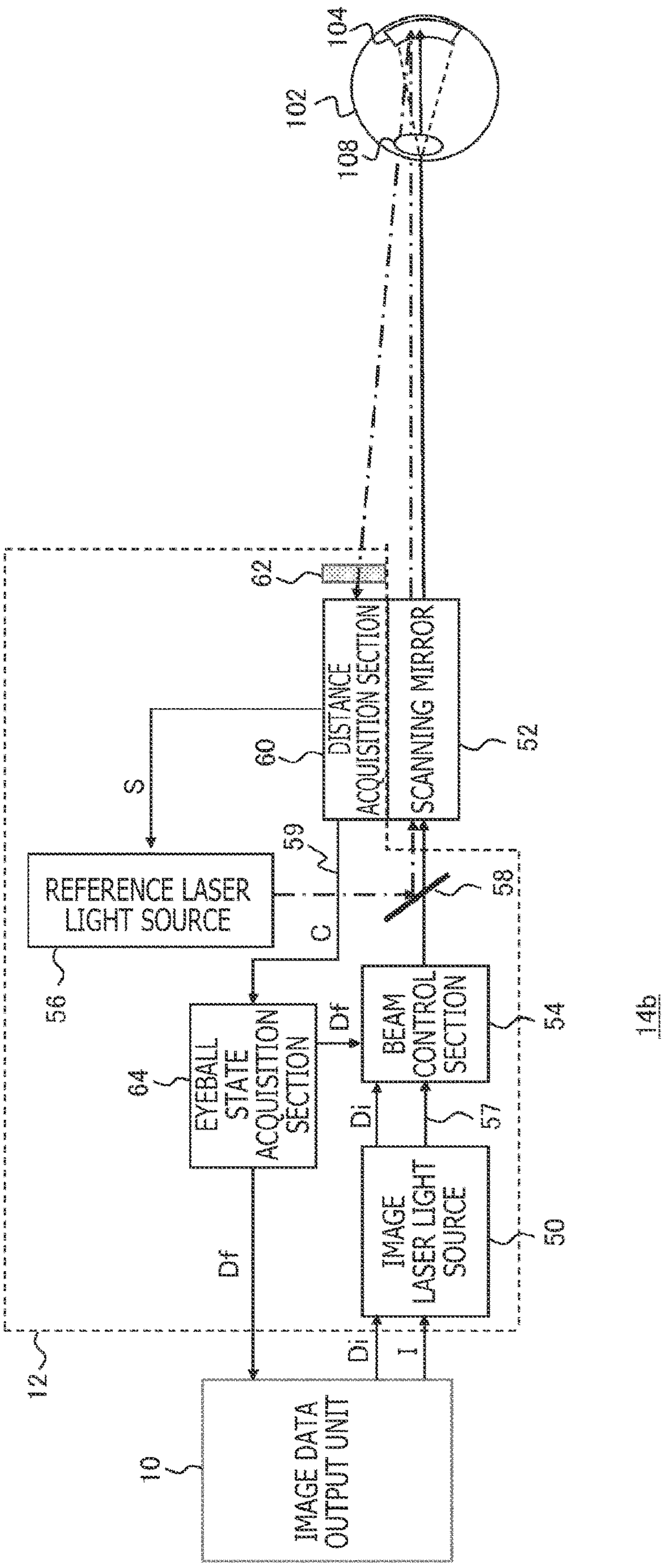
FIG. 12 is a diagram illustrating a configuration of an image display system according to the second embodiment.

FIG. 12 illustrates a configuration of an image display system according to the present embodiment. The configuration of the image display system according to the present embodiment is basically similar to the configuration depicted in FIG. 4. Constituent elements corresponding to those depicted in FIG. 4 are denoted by the same reference signs. More specifically, an image display system 14*b* includes the image data output unit 10, the light emission unit 12, and the scanning mirror 52. The light emission unit 12 includes the image laser light source 50, the beam control section 54, the reference laser light source 56, the beam splitter 58, the reference laser light transmission filter 62, the distance acquisition section 60, and the eyeball state acquisition section 64.

It should be noted that the image laser light source 50 and the reference laser light source 56 may be replaced by the image/reference laser light source 120 depicted in FIG. 10.

The configurations of the image laser light source 50 and reference laser light source 56 are basically similar to the configurations described in conjunction with the first embodiment. However, the reference laser light source 56 in the present embodiment continuously generates the pulse of the reference laser light 59 in parallel with emission of the image laser light 57. The distance acquisition section 60 detects the reflected reference laser light on a similar principle to the principle described in conjunction with the first embodiment, and thus determines the data set C, which includes the distances C1, C2, C3, . . . to the plurality of reflective surfaces of the eyeball 102.

Temporal changes in the distances C1, C2, C3, . . . can be acquired by continuously emitting the pulse of the reference laser light. When the crystalline lens thickness changes, the relevant distance values also change. Therefore, the distance acquisition section 60 determines the data set C, for example, at predetermined intervals and sequentially supplies the determined data set C to the eyeball state acquisition section 64. The eyeball state acquisition section 64 determines temporal changes in the thickness of the crystalline lens 108 according to the data set C. The eyeball state acquisition section 64 estimates a focal distance Df at predetermined intervals on the basis of the result of the determination and reports the estimated focal distance Df to the beam control section 54. The eyeball state acquisition section 64 may additionally report information regarding the focal distance Df to the image data output unit 10 as appropriate.

The beam control section 54 adjusts the image laser light 57 in such a manner that the image of an object at a position corresponding to the reported focal distance Df looks clear and that the image of an object at a distant position not corresponding to the focal distance Df looks blurry. Therefore, the beam control section 54 acquires depth information Di corresponding to a display image from the image data output unit 10 through the image laser light source 50. Subsequently, the beam control section 54 collates the depth information Di with the focal distance Df and determines a region of the image plane where the image is clarified and a region of the image plane where the image is blurred.

A resolution adjustment principle described in conjunction with the first embodiment can be applied as a method for clarifying and blurring images. More specifically, the beam control section 54 makes adjustments such that the beam state of image laser light representing an image varies from one image region to another. As a result of such adjustments, the resolution can be controlled with the pixels considered as the smallest units in order to express focal point changes that match changes in the crystalline lens. In the present embodiment, the image data output unit 10 may further acquire the information regarding the focal distance Df and vary the resolution from one set of image data to another according to the acquired focal distance information.

For example, the image data output unit 10 decreases, from the beginning, the resolution of a region to be blurred by the beam control section 54, and then generates display image data. As regards the region to be blurred by the adjustments of the beam state of the image laser light, visual recognition is not significantly affected even when an image generation process is simplified to decrease the resolution. Consequently, it is possible to reduce the load on the image generation process in the image data output unit 10 without causing image quality degradation. In this case, the image data output unit 10 collates the depth information Di corresponding to the display image, with the focal distance Df, determines the region where the image generation process can be simplified, and generates the display image.

Figure 13:
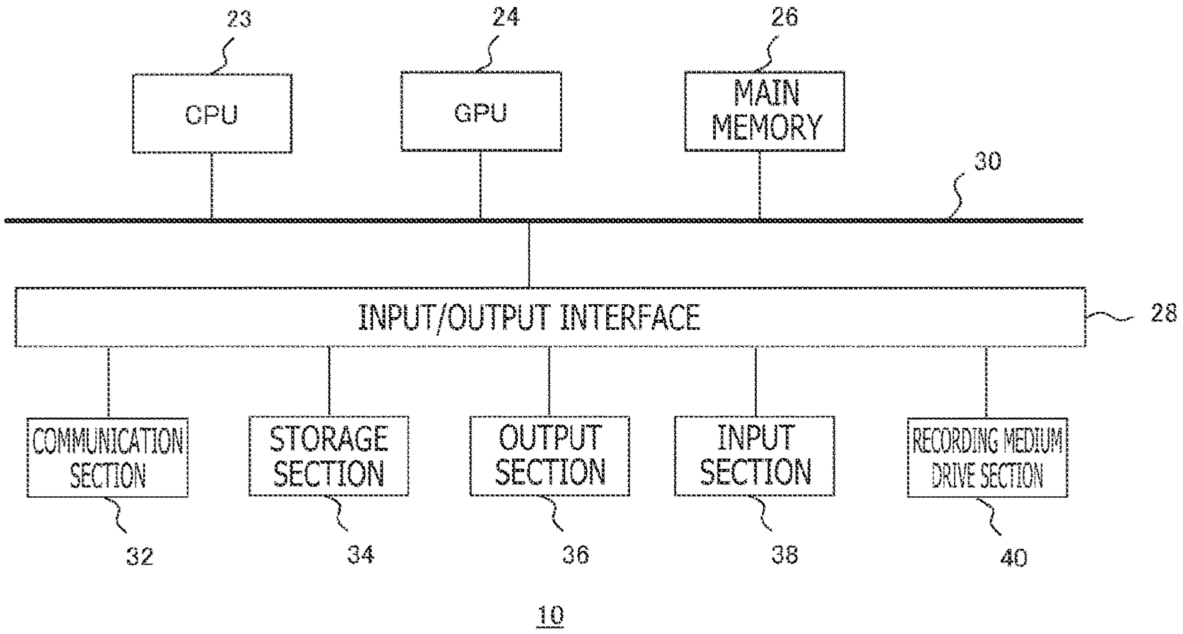
FIG. 13 is a diagram illustrating an internal circuit configuration of an image data output unit in the second embodiment.

FIG. 13 illustrates an internal circuit configuration of the image data output unit 10. The image data output unit 10 includes a central processing unit (CPU) 23, a graphics processing unit (GPU) 24, and a main memory 26. These constituent elements are interconnected through a bus 30. The bus 30 is further connected to an input/output interface 28.

The input/output interface 28 is connected to a communication section 32, a storage section 34, an output section 36, an input section 38, and a recording medium drive section 40. The communication section 32 establishes communication, for example, with a server. The storage section 34 includes, for example, a hard disk drive or a non-volatile memory. The output section 36 outputs data to the image laser light source 50. The input section 38 receives, as input, data from the eyeball state acquisition section 64. The recording medium drive section 40 drives a removable recording medium such as a magnetic disk, an optical disk, or a semiconductor memory. The communication section 32 includes a peripheral device interface such as a universal serial bus (USB) or Institute of Electrical and Electronics Engineers (IEEE) 1394, and a network interface such as a wired or wireless local area network (LAN).

The CPU 23 controls the whole of the image data output unit 10 by executing an operating system stored in the storage section 34. The CPU 23 also executes various programs that are read from a removable recording medium and loaded into the main memory 26 or that are downloaded through the communication section 32. The GPU 24 functions as a geometry engine and as a rendering processor, performs a drawing process according to a drawing command from the CPU 23, and outputs the result of the drawing process to the output section 36. The main memory 26 includes a random-access memory (RAM) and stores programs and data necessary for processing.

Figure 14:
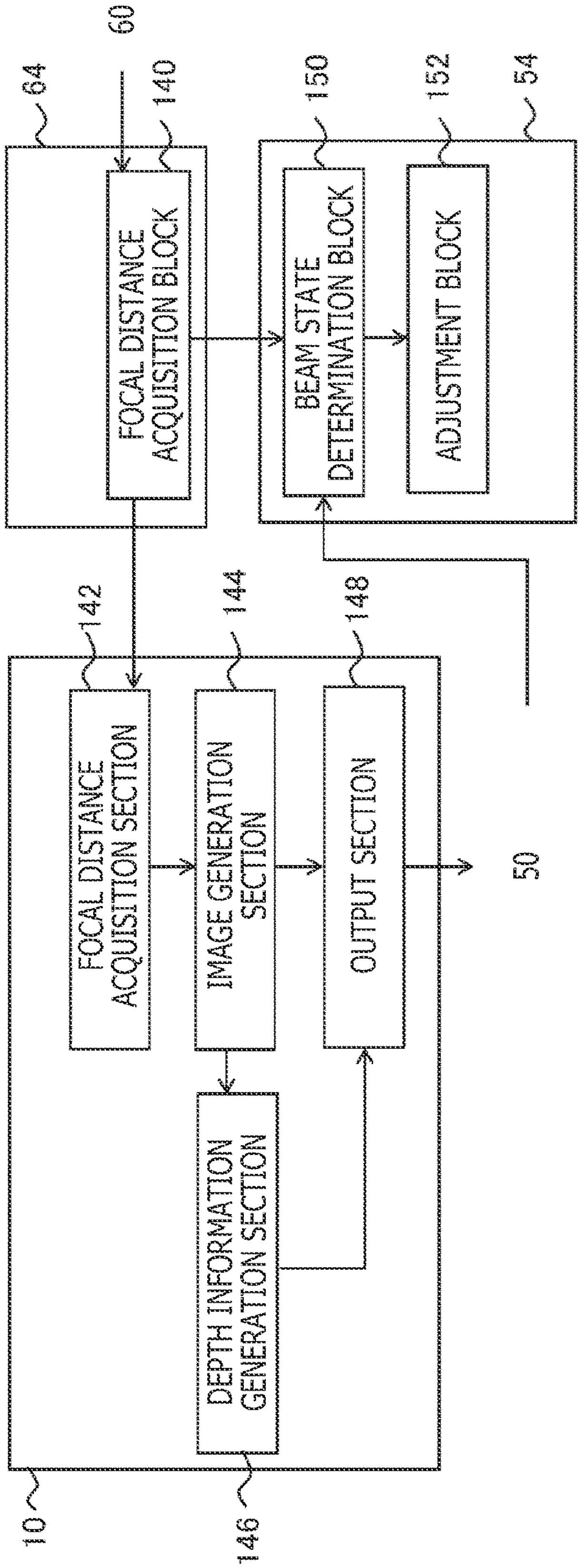
FIG. 14 is a diagram illustrating configurations of functional blocks of the eyeball state acquisition section, the image data output unit, and the beam control section in the second embodiment.

FIG. 14 illustrates configurations of functional blocks of the eyeball state acquisition section 64, image data output unit 10, and beam control section 54. The functional blocks depicted in FIG. 14 can be implemented by hardware such as the CPU 23, the GPU 24, and the main memory 26, which are depicted in FIG. 13, as well as various sensors and microprocessors, or implemented by software such as programs that are loaded from a recording medium into a memory and that perform various functions such as an information processing function, an image drawing function, a data input/output function, and a communication function. Hence, it will be understood by persons skilled in the art that the functional blocks may variously be implemented by hardware only, by software only, or by a combination of hardware and software. The method of implementing the functional blocks is not limited to a particular one.

It should be noted that the functional block configuration of the distance acquisition section 60 is not depicted in FIG. 14 because it is similar to the functional block configuration depicted in FIG. 5. The eyeball state acquisition section 64 includes a focal distance acquisition block 140. The focal distance acquisition block 140 estimates the focal distance on a real time basis by using the distance values supplied from the distance acquisition section 60. More specifically, the focal distance acquisition block 140 sequentially determines the thickness of the crystalline lens from the distance difference between the front and back surfaces of the crystalline lens, for example, at predetermined intervals, and estimates the focal distance at each time point according to the result of the thickness determination. Thus, the focal distance acquisition block 140 retains a focal distance table indicative of the association between the crystalline lens thickness and the focal distance, for example, in an internal memory.

For example, in a case where the eyeball is positioned in the laser light path at a distance of 5 cm from the laser light emitting port, the time lag Δt between the emission of reference laser light and the detection of the reflected reference laser light is determined as indicated below.

$$\Delta t=1/(3.0\times 10\ 8)[\text{m/sec}]\times 0.1\ [\text{m}]=0.33\ [\text{nsec}]$$

When the frame rate of the projection image is 30 fps (frame/sec), the number P of times the laser pulse is emitted per frame is determined as indicated below.

$$P=1/30\ [\text{fps}]/0.33\ [\text{nsec}]=5\times 10^8\ [\text{dots}]$$

When the resolution of the projection image is 1280×720 pixels, the number p of times the reference laser light is emitted per pixel is determined as indicated below.

$$p=5\times 10^8\ [\text{dots}]/(1280\times 720)[\text{pixel}]=108.5\ [\text{dots/pixel}]$$

Ideally, supposing that measurements are made approximately 500 times in a period of time required to measure a distance with practical accuracy and that the reflected laser light pulses can be detected by all light-receiving elements, it is sufficient to dispose approximately five light-receiving elements on the light-receiving surface of the distance acquisition section 60.

When the above-described configuration is adopted, the focal distance acquisition block 140 is able to acquire the data set C regarding distance values at significantly shorter intervals than frame display intervals and acquire the crystalline lens thickness with high temporal resolution at such shorter intervals. Consequently, even if the focal distance changes during a period of time when an image corresponding to one frame is projected, the beam state can be adjusted accordingly, so that the focus can be adjusted appropriately in an image. However, the frequency of beam state adjustments is not specifically limited. The beam state may be adjusted, for example, at one-frame intervals or longer intervals.

It should be noted that the distance acquisition section 60 may measure changes in the crystalline lens thickness by using a method other than the use of a dToF sensor. For example, a camera for capturing the image of an eyeball is adopted as the distance acquisition section 60. Then, the distance acquisition section 60 measures changes in the crystalline lens thickness on the basis of Purkinje-Sanson image changes in a captured image of the eyeball to which the reference laser light is emitted (refer to, for example, Japanese Patent Laid-open No. 2000-139841). In this case, it is sufficient if an additional path is provided such that the reference laser light obliquely enters the crystalline lens.

The image data output unit 10 includes a focal distance acquisition section 142, an image generation section 144, a depth information generation section 146, and an output section 148. The focal distance acquisition section 142 acquires information regarding the focal distance. The image generation section 144 generates a display target image. The depth information generation section 146 generates the depth information regarding an image. The output section 148 outputs the display image data and the depth information. The focal distance acquisition section 142 acquires the information regarding the focal distance from the eyeball state acquisition section 64 continuously, for example, at predetermined intervals.

The image generation section 144 generates frame data of a still image or video to be displayed. In this instance, the image generation section 144 may acquire image data that has generated in advance, for example, from an external device such as a server or from an internal storage device. Alternatively, the image generation section 144 may draw an image by itself with the use of a program and model data stored, for example, in the internal storage device. The depth information generation section 146 generates the depth information that indicates the distance distribution of objects to be represented in the plane of the image generated by the image generation section 144.

In a case where the image generation section 144 draws an image by itself, the depth information generation section 146 generates the depth information by acquiring, from the image generation section 144, distance information obtained during the drawing process. In a case where an image that has been generated in advance is to be reproduced, the depth information generation section 146 may acquire the depth information that is supplied in association with the relevant image data. Alternatively, the depth information generation section 146 may generate the depth information corresponding to an image that has been generated in advance, for example, by image analysis or deep learning.

In a case where the resolution of the image data itself is to be changed according to changes in the focal distance obtained from the crystalline lens, the image generation section 144 collates the depth information generated by the depth information generation section 146, with the focal distance information acquired by the focal distance acquisition section 142, and reflects the result of the collation in the image generation process. That is, the image generation section 144 generates an image in such a manner that the resolution of an object to be depicted in the image increases as the position of the object is closer to the focal distance (the resolution of the object decreases as the position of the object is farther away from the focal distance). Therefore, the image generation section 144 retains a resolution table indicative of the association between an object distance (depth) based on the focal distance and a target resolution value, for example, in an internal memory.

The image generation section 144 preferably reflects the focal distance information that has just been obtained, in the resolution of the image to be generated next. However, the rate of focal distance acquisition by the eyeball state acquisition section 64 and the rate of resolution distribution update by the image generation section 144 may be set independently of each other. In a case where the focal distance is not to be reflected in the image data, the function of the focal distance acquisition section 142 may be removed. The output section 148 associates data of the image generated by the image generation section 144 with data regarding the depth information generated by the depth information generation section 146, and outputs the resulting data to the image laser light source 50. In a case where a video is to be displayed, the output section 148 outputs data of the video at a predetermined frame rate.

The beam control section 54 includes a beam state determination block 150 and an adjustment block 152. The beam state determination block 150 determines the optimal value of the beam state. The adjustment block 152 adjusts the beam state of the image laser light according to the result of the determination. The beam state determination block 150 collates the depth information acquired through the image laser light source 50, with the focal distance information acquired from the eyeball state acquisition section 64, and thus determines the optimal value of the beam state for each pixel or region of the display image.

More specifically, the beam state determination block 150 determines the beam state in such a manner that the acquired visual acuity for an object to be depicted in an image increases as the position of the object is closer to the focal distance (the acquired visual acuity decreases as the position of the object is farther away from the focal distance). Therefore, the beam state determination block 150 retains a beam state table indicative of the association between an object distance (depth) based on the focal distance and a target beam state value, for example, in an internal memory.

The adjustment block 152 adjusts the image laser light by means similar to that described in conjunction with the first embodiment, in order to obtain the beam state determined by the beam state determination block 150. However, the adjustment block 152 in the present embodiment identifies which pixel in the display image is formed by the image laser light emitted from the image laser light source 50, and then adjusts the image laser light to obtain the beam state determined for the relevant pixel. It is desirable that, when the distribution of the beam state determined by the beam state determination block 150 changes in response to a change in the focal distance, the adjustment block 152 respond immediately and reflect such a change in the beam state.

FIG. 15 illustrates an example of the data structure of the resolution table that is internally retained by the image generation section 144. In the example of FIG. 15, a resolution table 160 includes data indicating the association between the range of distances with the focal distance as a reference point (starting point) and the target resolution value of an object positioned within the range. It should be noted that "High," "Medium," or "Low" is set as the target resolution value in FIG. 15. In practice, however, specific numerical values corresponding to high resolution, medium resolution, and low resolution are set. The original resolution of an image may be any one of the "High," "Medium," and "Low" depicted in FIG. 15.

For example, in a case where the original resolution is "High," the image generation section 144 adjusts the resolution only in such a direction as to decrease the resolution. In a case where the original resolution is "Medium," the image generation section 144 adjusts the resolution in such a direction as to either increase or decrease the resolution depending on the region. In a case where the original resolution is "Low," the image generation section 144 adjusts the resolution only in such a direction as to increase the resolution.

Further, it is assumed that the axis of "Distance Range" typically represents the depth direction from a virtual viewpoint with respect to an image. However, in a case, for example, where the motion of the user's eyeball can be acquired separately, the distance range may be set in another direction as well. For example, a gaze point detector may be added to the configuration of the image display system, and the distribution of the resolution may be set within the range of horizontal distances with a gaze point in an image as a reference point. The gaze point detector is a well-known device that emits reference light such as infrared rays to the eyeball and that identifies the gaze point from an eyeball motion on the basis of a captured image of the eyeball.

It should be noted that the distance acquisition section 60 and eyeball state acquisition section 64 in the present embodiment may act as the gaze point detector. More specifically, when light-receiving elements are two-dimensionally arrayed on the light-receiving surface of the distance acquisition section 60, the reflected reference laser light is indicated as an image expressing a two-dimensional brightness distribution. Hence, the eyeball state acquisition section 64 may identify the gaze point by acquiring the eyeball motion from the image expressing the two-dimensional brightness distribution.

Alternatively, the distance acquisition section 60 may acquire, as the two-dimensional distribution, the above-mentioned distance to the reflective surface according to the two-dimensional array of the light-receiving elements. Accordingly, the eyeball state acquisition section 64 may acquire the two-dimensional distribution of crystalline lens thicknesses. The crystalline lens thickness is greatest at the center of the crystalline lens, which corresponds to the optical axis, and decreases with a decrease in the distance to the edge of the crystalline lens. Hence, the eyeball state acquisition section 64 may detect the eyeball motion on the basis of changes in the two-dimensional distribution of crystalline lens thicknesses and may thus identify the gaze point.

According to the settings indicated in FIG. 15, the image of an object that is present within a range of less than 1 m from a position corresponding to the focal distance is expressed with high resolution, the image of an object that is present within a range of 1 m or more but less than 5 m from the position corresponding to the focal distance is expressed with medium resolution, and the image of an object that is present within a range of 5 m or more from the position corresponding to the focal distance is expressed with low resolution. When a distribution is given to data regarding the resolution according to the focal distance as described above, the image laser light can be adjusted according to changes in the resolution.

Accordingly, the image generation section 144 does not have to place unnecessary processing load on a region that is to be finally blurred by the beam state adjustment. Further, when a region close to a position corresponding to the focal distance is surely provided with high resolution in the image data, the effect of the beam state adjustment can clearly be expressed without being negated. It should be noted that numerical values depicted in FIG. 15 are merely examples. The numerical values may be set with finer granularity. Moreover, as long as the target resolution value can be derived from the distance range, the data to be used for such derivation is not limited to a table and may alternatively be, for example, a calculation formula.

FIG. 16 illustrates an example of the data structure of the beam state table that is internally retained by the beam state determination block 150. In the example depicted in FIG. 16, the beam state table 170 includes data indicating the association between the range of distances with the focal distance as a reference point (starting point) and the target beam state value of image laser light at the time of expressing an object within the above-mentioned range. As the beam state, the depicted example indicates the beam diameter and the numerical aperture corresponding to the divergence angle. Alternatively, however, only one of them may be indicated as the beam state.

As indicated, for example, in FIG. 2, when the beam diameter is 1.5 mm, the beam spot on the retina is theoretically minimized under certain conditions. Therefore, in a case where only the beam diameter is to be adjusted, setup is made such that the beam diameter is 1.5 mm in the vicinity of a position corresponding to the focal distance and increases or decreases with an increase in the distance from the position corresponding to the focal distance. In a case where only the divergence angle is to be adjusted, setup is made such that, for example, the beam diameter is fixed at 1.5 mm and that the divergence angle increases with an increase in the distance from the position corresponding to the focal distance.

In a case where both the beam diameter and the divergence angle are to be adjusted, both of them are regarded as variables. Then, experiments or calculations are performed to determine the combination of the beam diameter and the divergence angle in such a manner that the distribution of resolution can visually be recognized without a sense of discomfort, and the association between the beam diameter and the divergence angle is defined. The beam state determination block 150 references the beam state table 170 to determine the optimal beam state for each pixel according to the focal distance which is acquired by the focal distance acquisition block 140 of the eyeball state acquisition section 64 on a real time basis, and to the depth information outputted from the image data output unit 10. Then, the beam state determination block 150 reports the determined optimal beam state to the adjustment block 152.

It should be noted that the contents of the beam state table 170 may be changed according to the user's unaided visual acuity. As described in conjunction with the first embodiment, the beam state where the highest resolution is visually recognized varies with the user's unaided visual acuity. Therefore, when the constituent elements used in the present embodiment are combined with those used in the first embodiment, setup can be made such that an object placed at the focal distance is visually recognized with the highest resolution irrespective of unaided visual acuity, and that, with such a state described above as a reference state, a distant object looks appropriately blurry.

In the above case, the beam state determination block 150 retains a plurality of beam state tables associated with unaided visual acuity, for example, in an internal memory. Then, the beam state determination block 150 first acquires the user's unaided visual acuity as described in conjunction with the first embodiment, and reads out the beam state table associated with the acquired user's unaided visual acuity. Subsequently, the adjustment block 152 uses the read-out beam state table to adjust the beam state according to the focal distance.

The setup of "Distance Range" in the depicted beam state table 170 may be made only in the depth direction as described in conjunction with the resolution table 160 depicted in FIG. 15. Alternatively, such setup may be made additionally in a direction other than the depth direction. Further, the depicted numerical values are merely examples and may be set with finer granularity. As long as the target beam state value can be derived from the distance range, the data to be used for such derivation is not limited to a table and may alternatively be, for example, a calculation formula.

FIGS. 17A and 17B schematically illustrate a display target image and a display resulting from the beam state adjustment. FIG. 17A illustrates an example of image data outputted from the image data output unit 10. In this example, the display target is a video image of a car that is travelling ahead within the field of view of a user who is playing a car race game. The image data output unit 10 generates data of a frame 180 of the video image and outputs the generated data at a predetermined rate. The image data output unit 10 further outputs data 182 regarding the depth information corresponding to the frame 180.

In the above example, the data 182 regarding the depth information is in the form of a depth image in which the distance values of an object appearing in the frame 180 are expressed as pixel values with brightness that increases with a decrease in the distance values. However, the data format of depth information is not limited to a particular format. FIG. 17B illustrates an image that is visually recognized by the user as the result of the beam state adjustment by the beam control section 54. The image laser light source 50 acquires the data of the frame 180 and sequentially generates laser light corresponding to each pixel.

The beam control section 54 references the beam state table according to the information regarding the user's focal distance that has just been obtained, and adjusts the beam state in such a manner that the resolution (acquired visual acuity) varies with the distance from a position corresponding to the focal distance. As a result, while the user focuses on a car 186*a* in front, the car 186*a* and its surroundings are clearly visible as indicated in a display image 184*a*, but a car 186*b* in the back and its surroundings look blurry. While the user focuses on the car 186*b* in the back, the car 186*b* and its surroundings are clearly visible as indicated in a display image 184*b*, but the car 186*a* in front and its surroundings look blurry.

It should be noted that, in the depicted example, resolution adjustments are not made to the data of the frame 180 that is outputted from the image data output unit 10. However, as mentioned earlier, the distribution may be given to the resolution of the data of the frame 180 as depicted in FIG. 17B.

According to the present embodiment described above, in the image display system which projects an image onto the retina by using the laser beam scanning method, the reference laser light is emitted to the eyeball in parallel with emission of the image laser light, and the reflected reference laser light is detected, thereby acquiring the state of the eyeball. More specifically, the image display system measures the thickness of the user's crystalline lens and estimates the focal distance on the basis of the result of measurement on a real time basis. The image display system controls the beam state on the basis of the estimated focal distance in such a manner that the resolution (acquired visual acuity) varies in the image plane. Thus, an appearance similar to the appearance in the real world can be reproduced on a display. This can resolve the convergence-accommodation conflict.

The present disclosure has been described above on the basis of the embodiments. It is to be understood by persons skilled in the art that the foregoing embodiments are illustrative, that a combination of the constituent elements and processes described in conjunction with the foregoing embodiments can be variously modified, and that such modifications can be made without departing from the spirit and scope of the present disclosure.

For example, in the first embodiment, the reference laser light is emitted to measure the numerical values of the crystalline lens thickness and other structural properties of the eye, and then, the unaided visual acuity is estimated to determine the optimal beam state. Alternatively, however, the unaided visual acuity may also be acquired by other means. For example, the unaided visual acuity may be inputted by the user through an undepicted input device. In such a case, for example, the image data output unit 10 may use the image laser light to display an unaided visual acuity input screen prompting the user to input data, and the eyeball state acquisition section 64 may receive the data inputted by the user. As long as the same process is subsequently performed as described in conjunction with the first embodiment, the resulting effect is similar to the effect obtained in the first embodiment.

Further, in the second embodiment, the reference laser light is emitted to measure changes in the crystalline lens thickness and estimate the focal distance, and the beam state is thus changed. Alternatively, however, in a case where the image display system includes the gaze point detector as mentioned earlier, the beam state may be changed only on the basis of the position of the gaze point in the image plane. In this case, for example, the beam control section 54 adjusts the beam state in such a manner that the highest acquired visual acuity is obtained in a region within a predetermined range including the gaze point in the image plane, and that the acquired visual acuity decreases with an increase in the distance from the gaze point.

The above alternative can also give a user a sense that a spot viewed by the user is in focus, and makes it possible to reduce discomfort caused by the convergence-accommodation conflict, in a simplified manner. It should be noted that, as mentioned earlier, the distance acquisition section 60 and the eyeball state acquisition section 64 may have the function of the gaze point detector. Also, in this case, the image data output unit 10 may generate image data by changing the distribution of resolution in the image plane in correspondence with the beam state adjustment. This reduces the load on the image generation process without significantly affecting visual recognition.

What is claimed is:

1. An image display system comprising:

a light emitter comprising:

an image laser light source configured to generate image laser light indicative of a display image based on image data;

a reference light source configured to emit laser light to an eye;

one or more sensors configured to detect the reference laser light reflected from the eye and further configured to acquire distances to reflective surfaces of the eye according to a result of the detection;

a scanning mirror configured to reflect the image laser light in such a manner that a destination of the image laser light is two-dimensionally scanned over a retina in the eye, and further configured to reflect and deliver the reference laser light to the eye; and a beam controller comprising at least either:

a beam expander configured to adjust a beam diameter of the image laser light; or a liquid lens configured to adjust a beam divergence angle of the image laser light, wherein the beam controller is configured to:

receive visual acuity information of the eye, wherein the visual acuity information comprises information according to a distance between the reflective surfaces;

cause at least either the beam expander or the liquid lens to adjust, according to the visual acuity information, at least either the beam diameter or the beam divergence angle of the image laser light; and project the image laser light onto the retina in the eye.

2. The image display system according to claim 1, wherein the reference light source is configured to emit the reference laser light to the eye along a light path of the image laser light.

3. The image display system according to claim 1, wherein the visual acuity information comprises a crystalline lens thickness or an eye axial length to estimate the visual acuity of the eye; and wherein the beam controller is further configured to adjust at least either the beam diameter or the beam divergence angle of the image laser light according to the visual acuity.

4. The image display system according to claim 1, wherein the visual acuity information comprises a crystalline lens thickness to estimate a focal distance of the eye; and wherein the beam controller is further configured to change at least either the beam diameter or the beam divergence angle of the image laser light on an image plane according to a relationship between the focal distance and a distance to an object in a three-dimensional space to be displayed.

5. The image display system according to claim 4, wherein the beam controller is configured to adjust at least either the beam diameter or the beam divergence angle in such a manner that an object that is present in the three-dimensional space and that is positioned within a predetermined range from a position corresponding to the focal distance is visually recognized with a higher resolution than other objects in the three-dimensional space.

6. The image display system according to claim 4, further comprising:

an image data output unit comprising:

one or more processors; and a memory device storing instructions that, when executed by the one or more processors, cause the image data output unit to:

change a resolution on the image plane according to the relationship between the focal distance and the distance to the object in the three-dimensional space; and generate data of the display image.

7. The image display system of claim 4, further comprising:

a visual acuity table comprising data indicating an association between a crystalline lens thickness and a visual acuity, and wherein the visual acuity is estimated from the visual acuity table using the crystalline lens thickness.

8. The image display system according to claim 1, wherein the visual acuity information comprises a data set regarding the distances to the reflective surfaces, at intervals shorter than intervals at which a frame of a video is displayed by the image laser light, and a focal distance estimated using the data set.

9. The image display system according to claim 1, wherein the one or more sensors are configured to detect the reference laser light reflected from the eye, at a position circumscribing an outlet port that is configured to allow the image laser light and the reference laser light reflected from the scanning mirror to be emitted.

10. The image display system according to claim 1, wherein the visual acuity information comprises a gaze point comprising a two-dimensional distribution of crystalline lens thicknesses, and wherein the beam controller is configured to change at least either the beam diameter or the beam divergence angle of the image laser light on an image plane according to the gaze point.

11. An image display method performed by an image display system, the image display method comprising:

generating image laser light indicative of a display image based on image data;

emitting reference laser light to an eye with a reference light source;

detecting the reference laser light reflected from the eye with one or more sensors;

acquiring distances to reflective surfaces of the eye according to a result of the detection;

reflecting, with a scanning mirror, the image laser light in such a manner that a destination of the image laser light is two-dimensionally scanned over a retina in the eye, and the reference laser light to deliver the reference laser light to the eye;

receiving, by a beam controller, visual acuity information regarding the eye, wherein the visual acuity information comprises information according to a distance between the reflective surfaces;

causing at least either a beam expander or a liquid lens of the beam controller to adjust, according to the visual acuity information, at least either a beam diameter or a beam divergence angle of the image laser light; and projecting the image laser light onto the retina in the eye.

12. The image display method of claim 11, wherein the visual acuity information comprises a gaze point comprising a two-dimensional distribution of crystalline lens thicknesses; wherein the method further comprises changing, by the beam controller, at least either the beam diameter or the beam divergence angle of the image laser light on an image plane according to the gaze point.

13. The image display method of claim 11, wherein the visual acuity information comprises a crystalline lens thickness or an eye axial length to estimate the visual acuity of the eye; wherein the method further comprises adjusting, by the beam controller, at least either the beam diameter or the beam divergence angle of the image laser light according to the visual acuity.

14. The image display method of claim 11, wherein the visual acuity information comprises a data set regarding the distances to the reflective surfaces, at intervals shorter than intervals at which a frame of a video is displayed by the image laser light, and a focal distance estimated using the data set.

15. The image display method of claim 11, wherein the visual acuity information comprises a crystalline lens thickness to estimate a focal distance of the eye; the method further comprising changing, by the beam controller, at least either the beam diameter or the beam divergence angle of the image laser light on an image plane according to a relationship between the focal distance and a distance to an object in a three-dimensional space to be displayed.

16. The image display method of claim 15, wherein the beam controller is configured to adjust at least either the beam diameter or the beam divergence angle in such a manner that an object that is present in the three-dimensional space and that is positioned within a predetermined range from a position corresponding to the focal distance is visually recognized with a higher resolution than other objects in the three-dimensional space.

17. The image display method of claim 15, further comprising:

estimating the visual acuity from a visual acuity table using the crystalline lens thickness, wherein the visual acuity table comprises data indicating an association between a crystalline lens thickness and a visual acuity.

* * * * *